United States Patent
Lin et al.

(10) Patent No.: US 10,980,284 B2
(45) Date of Patent: Apr. 20, 2021

(54) ELECTRONIC CIGARETTE ATOMIZER EMPLOYING VERTICAL CERAMIC ATOMIZING UNIT

(71) Applicant: Guangrong Lin, Guangdong (CN)

(72) Inventors: Guangrong Lin, Guangdong (CN); Xianbin Zheng, Guangdong (CN)

(73) Assignee: Guangrong Lin, Shenzhen (CN)

( * ) Notice: Subject to any disclaimer, the term of this patent is extended or adjusted under 35 U.S.C. 154(b) by 295 days.

(21) Appl. No.: 16/322,119

(22) PCT Filed: Jun. 15, 2017

(86) PCT No.: PCT/CN2017/088467
§ 371 (c)(1),
(2) Date: Jan. 31, 2019

(87) PCT Pub. No.: WO2018/001107
PCT Pub. Date: Jan. 4, 2018

(65) Prior Publication Data
US 2019/0174832 A1    Jun. 13, 2019

(30) Foreign Application Priority Data

Jul. 1, 2016   (CN) .......................... 201610517015.4

(51) Int. Cl.
*A24F 47/00* (2020.01)
*A61M 11/04* (2006.01)
(Continued)

(52) U.S. Cl.
CPC ............ *A24F 47/008* (2013.01); *A24F 40/10* (2020.01); *A24F 40/46* (2020.01); *A24F 47/00* (2013.01); *A61M 11/042* (2014.02); *A61M 15/06* (2013.01)

(58) Field of Classification Search
None
See application file for complete search history.

(56) References Cited

U.S. PATENT DOCUMENTS 9,226,526 B2 *  1/2016  Liu ........................ A24F 47/008
9,364,024 B2 *  6/2016  Liu ........................ A24F 47/008
(Continued)

FOREIGN PATENT DOCUMENTS

| CN | 104223368 A | 12/2014 |
| CN | 203969206 U | 12/2014 |
| CN | 206137192 U | 5/2017 |

OTHER PUBLICATIONS

International Search Report of PCT Patent Application No. PCT/CN2017/088467 dated Aug. 30, 2017.

*Primary Examiner* — Ross N Gushi

(57) ABSTRACT

An electronic cigarette atomizer employing a vertical ceramic atomizing unit, the atomizing unit (6) includes a ceramic atomizing rod (61) made from a ceramic material, a heating wire (62) wound around the ceramic atomizing rod (61), and a lead wire (63) connected to both ends of the heating wire (62); the ceramic atomizing rod (61) is vertically disposed in an atomizing seat (5), an upper-end surface of the ceramic atomizing rod (61) is in direct contact with a cigarette liquid permeation sheet (4) and can absorb and conduct electronic cigarette liquid from the cigarette liquid permeation sheet (4) to a portion around which the heating wire (62) is wound. The electronic cigarette atomizer of the present invention employs a plurality of vertical ceramic atomizing units (6), which gives an atomization effect of a large smoke volume and avoids the production of a burnt odor.

12 Claims, 7 Drawing Sheets

(51) Int. Cl.
*A61M 15/06* (2006.01)
*A24F 40/10* (2020.01)
*A24F 40/46* (2020.01)

(56) References Cited

U.S. PATENT DOCUMENTS 9,848,653 B2 * 12/2017 Lin .................. A24F 47/008
9,913,496 B2 * 3/2018 Lin .................. A24F 47/008

* cited by examiner

ELECTRONIC CIGARETTE ATOMIZER EMPLOYING VERTICAL CERAMIC ATOMIZING UNIT

FIELD OF THE INVENTION

The present invention relates to the technical field of electronic cigarettes and particularly relates to an electronic cigarette atomizer employing a vertical ceramic atomizing unit.

BACKGROUND OF THE INVENTION

Traditional tobacco-type cigarettes contain tar, which is easily inhaled during smoking, posing significant health hazards. Electronic cigarettes produce smoke by heating a cigarette liquid with an atomizer. As the electronic cigarette liquid does not contain any tar, electronic cigarettes are gradually used as a replacement for traditional cigarettes.

In order to increase the amount of smoke inhaled in one puff of an electronic cigarette, an atomizer with dual heating wires are employed. Due to space limitations, the atomizers with dual-heating wires in existing electronic cigarettes usually adopt an arrangement in which the dual-heating wires are provided at the same central axis in the atomizer chamber. Air flowing into such a structure needs to pass through the two heating wires consecutively; it is not able to be in contact with the two heating wires simultaneously. As a result, the atomization effect is reduced. In addition, an atomizing core or atomizing rod in existing atomizing units is generally made from a soft material such as a fiber material. When in frequent use, the atomizing rod is prone to burning and deformation due to a high temperature generated by the atomizing unit. Consequently, the atomizing unit is not in sufficient contact with the air flow, affecting the atomization of the electronic cigarette liquid. In addition, the deformation of the atomizing rod may also lead to the burning of the atomizing seat, which produces a burnt odor, damaging user experience.

SUMMARY OF THE INVENTION

The objective of the present invention is to provide an electronic cigarette atomizer which employs a vertical ceramic atomizing unit. The electronic cigarette atomizer adopts a double atomizing unit, which gives an atomization effect with a large smoke amount and avoids the production of a burnt odor due to high-temperature burning. As a result, the user experience can be significantly improved.

The technical solution of the present invention achieved as follows: an electronic cigarette atomizer employing a vertical ceramic atomizing unit, which comprises an outer tube that is provided with a suction hole at its upper end and an opening at its lower end; the electronic cigarette atomizer further comprises a liquid storage cup, a porous supporting sheet, a cigarette liquid permeation sheet, an atomizing seat, an atomizing unit, a sealed connection joint, and a power connector sheathed in the outer tube consecutively from top to bottom; the liquid storage cup is closed at its upper end and opened at its lower end; the porous supporting sheet is horizontally attached to an inner wall of a lower end of the liquid storage cup; the atomizing unit includes a ceramic atomizing rod made from a ceramic material, a heating wire wound around the ceramic atomizing rod, and a lead wire connected to both ends of the heating wire; the atomizing seat is a high-temperature resistant tubular body with a vapor outlet provided at its wall, an upper-end surface of the atomizing seat presses the cigarette liquid permeation sheet tightly against the porous supporting sheet; the ceramic atomizing rod is vertically disposed in the atomizing seat, an upper-end surface of the ceramic atomizing rod is in direct contact with the cigarette liquid permeation sheet and can absorb and conduct electronic cigarette liquid from the cigarette liquid permeation sheet to a portion around which the heating wire is wound; the sealed connection joint is in sealed connection with the atomizing seat and the power connector, the inside of the sealed connection joint is provided with a through hole in an axial direction; the power connector is sheathed in a lower end of the outer tube and rests against an inner wall of the outer tube.

Preferably, one supporting vertical groove is provided in each of two inner walls at both sides of the vapor outlet at an upper end of the atomizing seat; each of the supporting vertical groove is installed with one atomizing unit.

Preferably, one supporting vertical groove is provided in each of three inner walls at both sides of the vapor outlet and opposite the vapor outlet at an upper end of the atomizing seat; each of the supporting vertical groove is installed with one atomizing unit.

Preferably, an atomizing seat cover is provided on the upper-end surface of the atomizing seat; the atomizing seat cover is provided with a cover hole at a position corresponding to the supporting vertical groove; the ceramic atomizing rod protrudes from the cover hole.

Preferably, the heating wire of each of the atomizing unit is parallelly connected to a power source.

Preferably, the ceramic atomizing rod has a cylindrical shape and is provided with an atomizing rod through hole at its central axis; a groove is provided on the upper-end surface of the ceramic atomizing rod along a diameter of the upper-end surface of the ceramic atomizing rod; the heating wire winds around an outer wall of the ceramic atomizing rod; the lead wire which is connected to an upper end of the heating wire is disposed in the groove and is led downwards through the atomizing rod through hole; another lead wire is led downwards along the outer wall of the ceramic atomizing rod.

Preferably, the ceramic atomizing rod has a cylindrical shape and is provided with an atomizing rod through hole at its central axis; a groove is provided on the upper-end surface of the ceramic atomizing rod along a diameter of the upper-end surface of the ceramic atomizing rod; the heating wire winds around an inside of the ceramic atomizing rod and is fused integrally therewith; the lead wire of the heating wire projects out of the atomizing rod and is led downwards.

Preferably, the liquid storage cup is provided with a rectangular notch at its lower end wall; an surface of the liquid storage cup is provided with a vapor groove in an axial direction and at the same circumferential position as the rectangular notch; the porous supporting sheet and the cigarette liquid permeation sheet are horizontally disposed and are attached to an inner wall of the liquid storage cup, above the rectangular notch; the atomizing seat is sheathed in the liquid storage cup and rest against an inner wall where the rectangular notch is located; the vapor outlet of the atomizing seat overlaps with the rectangular notch of the liquid storage cup; a heat insulating tube is provided between an outer wall of the liquid storage cup at a position of the rectangular notch, part of an outer wall of the sealed connection joint, part of an outer wall of an upper end of the power connector, and the inner wall of the outer tube.

Preferably, a lower end surface of the atomizing seat is provided with two legs, an upper-end surface of the sealed connection seat is provided with two grooved portions to accommodate the legs of the atomizing seat; a cavity is provided at a center of the upper-end surface of the sealed connection joint, a circular groove is provided at a bottom of the cavity at a rim of the through hole.

Preferably, the power connector includes a tubular body which is provided with an annular shoulder at its lower end; an electrode holder which is a hollow tube is inserted into the tubular body at an upper end of the tubular body; a thread is provided at an outer wall of a lower end of the electrode holder; a radial blocking ring is provided at an inner wall of the tubular body; an insulating holder is inserted into a central through hole of the blocking ring; a nail electrode is inserted into the insulating holder, the nail electrode is provided with an electrode through hole at a center thereof.

The electronic cigarette atomizer of the present invention has a plurality of vertical ceramic atomizing units provided at the inner wall of the atomizing cavity of the atomizing seat. This arrangement allows the air entering into the atomizing cavity to be in contact with the heating wires of both atomizing units simultaneously, which gives an atomization effect of a large smoke volume and avoids the production of a burnt odor due to the high-temperature burning of the atomizing seat. As a result, user experience can be significantly improved.

DETAILED DESCRIPTION OF THE ILLUSTRATED EMBODIMENTS

Best Mode for Carrying Out the Present Invention

The present invention will be further described hereafter with reference to the embodiments and accompanying drawings.

Figure 1:
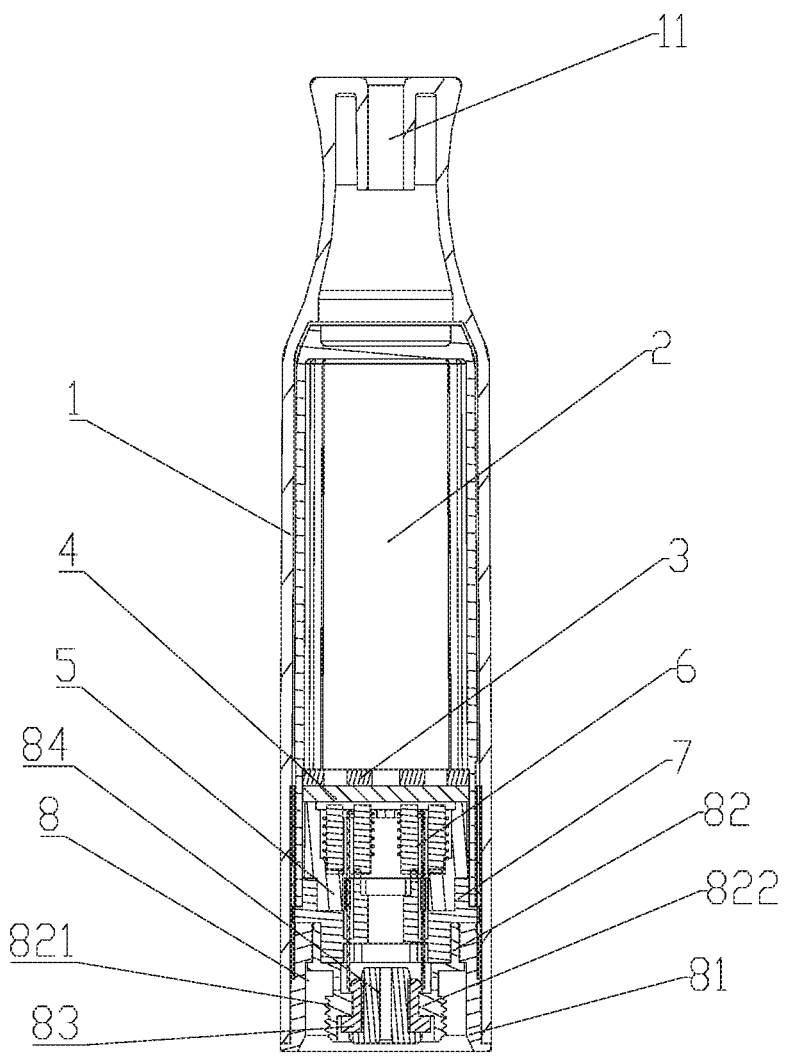
FIG. 1 is a cross-sectional view of embodiment 1 of the present invention.

The present invention relates to an electronic cigarette atomizer that employs a vertical ceramic atomizing unit. For the convenience of the following description, the electronic cigarette atomizer is placed vertically with its suction hole is facing upwards (as shown in FIG. 1). The terms "top", "bottom", "upper end", "lower end" are used to describe the positional relationships of the components when the electronic cigarette atomizer is placed vertically.

Figure 2:
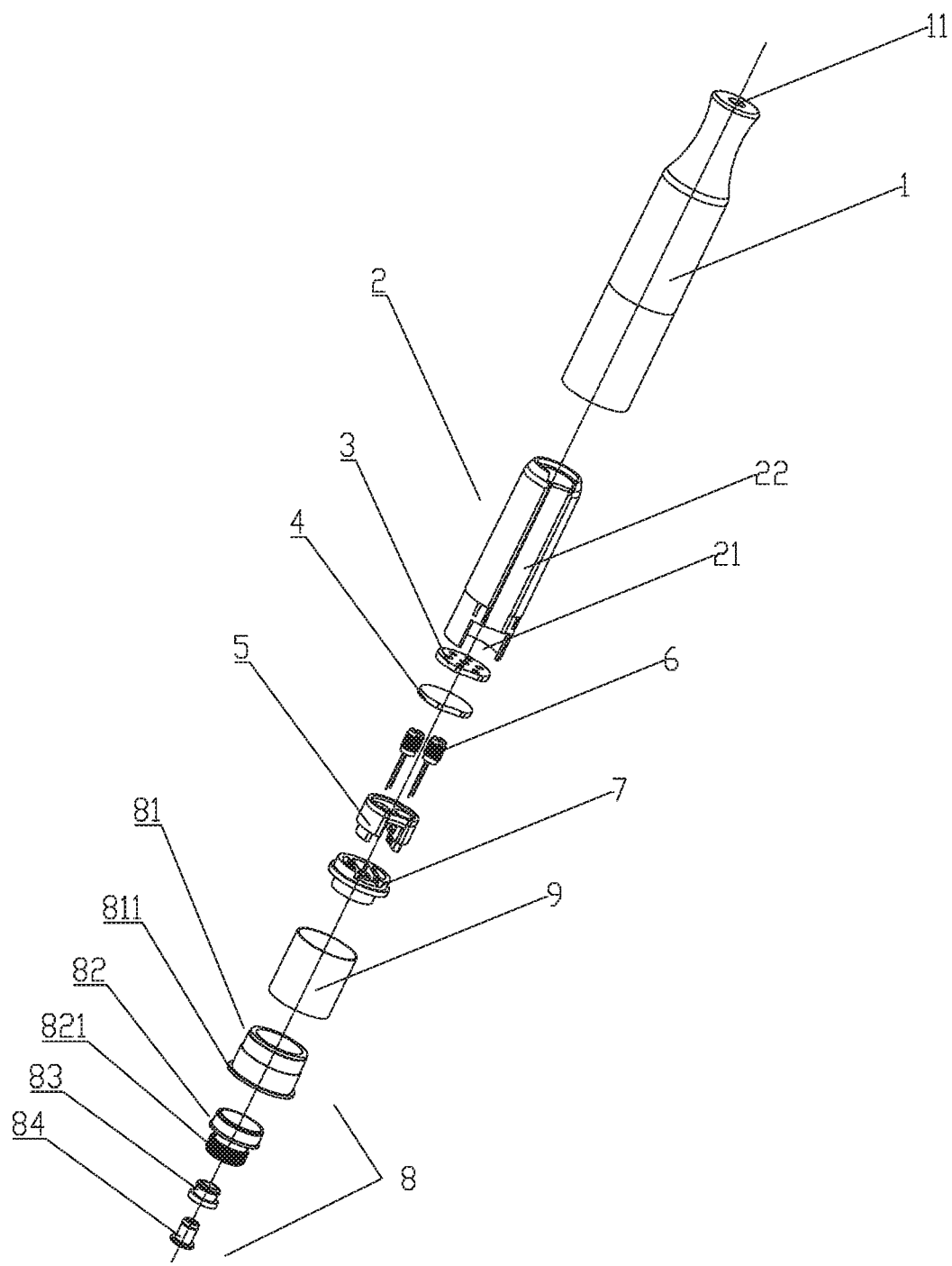
FIG. 2 is an exploded view of embodiment 1 of the present invention.

As shown in FIG. 1 and FIG. 2, the electronic cigarette atomizer which employs a vertical ceramic atomizing unit of the present invention comprises an outer tube 1 which is provided with a suction hole 11 at its upper end and an opening at its lower end; the electronic cigarette atomizer further comprises a liquid storage cup 2, a porous supporting sheet 3, a cigarette liquid permeation sheet 4, an atomizing seat 5, an atomizing unit 6, a sealed connection joint 7, and a power connector 8 inserted into the outer tube 1 consecutively from top to bottom. The liquid storage cup 2 is used to store the electronic cigarette liquid. The porous supporting sheet 3 is horizontally attached to the inner wall of a lower end of the liquid storage cup and is plugged into the opening of the liquid storage cup 2. The porous supporting sheet 3 is provided with a plurality of small holes for the electronic cigarette liquid to slowly flow out from the liquid storage cup 2. The porous supporting sheet 3 also serves to fix and support the cigarette liquid permeation sheet 4. The cigarette liquid permeation sheet 4 is closely attached to the porous supporting sheet 3 and is generally made from porous, heat resisting materials of low permeability. During smoking, negative pressure is generated in the atomizing seat 5, which allows the electronic cigarette liquid contained in the liquid storage cup 2 to permeate through the cigarette liquid permeation sheet 4. When the user is not smoking, the pressure inside and outside the liquid storage cup 2 is balanced, the cigarette liquid permeation sheet 4 prevents the cigarette liquid from leaking out of the liquid storage cup 2.

As shown in FIGS. 1-8, the atomizing seat 5 is a high-temperature resistant tubular body with a vapor outlet 51 provided at its wall. The upper-end surface of the atomizing seat presses the cigarette liquid permeation sheet 4 tightly against the porous supporting sheet 3. A ceramic atomizing rod 61 is vertically disposed in the atomizing seat 5, the upper-end surface of the ceramic atomizing rod 61 is in direct contact with the cigarette liquid permeation sheet 4 and can absorb and conduct the electronic cigarette liquid from the cigarette liquid permeation sheet 4 to the portion around which a heating wire 62 is wound. The sealed connection joint 7 is in sealed connection with the atomizing seat 5 and the power connector 8. The term "sealed connection" means that the end surfaces are sealed against each other. The inside of the sealed connection joint 7 is axially provided with a through hole 71. The power connector 8 is inserted into the inner wall of the lower end of the outer tube 1.

As shown in FIGS. 1 and 2, the liquid storage cup 2 is provided with a rectangular notch 21 at its lower end wall. The outer surface of the liquid storage cup 2 is provided with a vapor groove 22 in the axial direction and at the same circumferential position as the rectangular notch 21. The porous supporting sheet 3 and the cigarette liquid permeation sheet 4 are horizontally disposed and are attached to the inner wall of the liquid storage cup 2, above the rectangular notch 21. The atomizing seat 5 is sheathed to the liquid storage cup 2 and rest against an inner wall where the rectangular notch 21 is located; the vapor outlet 51 of the atomizing seat 5 overlaps with the rectangular notch 21 of the liquid storage cup. A heat insulating tube 9 is provided in the liquid storage cup 2, between the outer wall of the liquid storage cup 2 at the position of the rectangular notch 21, part of the outer wall of the sealed connection joint 7, part of the outer wall of the upper end of the power connector 8, and the inner wall of the outer tube 1.

As shown in FIGS. 1 and 2, the atomizing seat 5 abuts the inner wall of the liquid storage cup 1 at the position of the rectangular notch 21; the vapor outlet 51 of the atomizing seat 5 overlaps with the rectangular notch 21 of the liquid storage cup 2. In this way, the smoke generated by the atomizing unit can be discharged through the vapor outlet 51 (rectangular notch 21). The smoke then passes through a smoke discharge channel enclosed by the vapor groove 22 and the inner wall of outer tube 1, finally flows into the user's mouth through the suction hole 11 of the outer tube.

Figure 3:
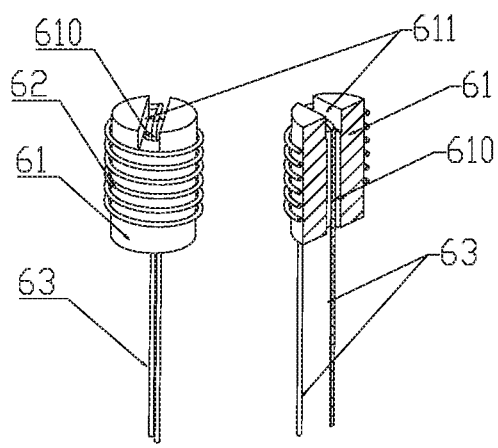
FIG. 3 is a perspective, cross-sectional view and a structural diagram of an atomizing unit according to embodiment 1 of the present invention.

As shown in FIG. 3, the atomizing unit 6 includes a ceramic atomizing rod 61 made from a ceramic material, a heating wire 62 wound around the ceramic atomizing rod 61, and lead wires 63 respectively connected to both ends of the heating wire 62. The ceramic atomizing rod 61 has a cylindrical shape and is provided with an atomizing rod through hole 610 at its central axis. A groove 611 is provided on the upper-end surface of the ceramic atomizing rod 61 along the diameter of the upper-end surface. The heating wire 62 winds around the outer wall of the ceramic atomizing rod 61. The lead wire 63 which is connected to the upper end of the heating wire 62 is disposed in the groove 611 and is led downwards through the atomizing rod through hole 610; the other lead wire 63 is led downwards along the outer wall of the ceramic atomizing rod 61. In this embodiment, the heating wires 62 of the two atomizing units 6 are parallelly connected to the power source. The atomizing unit 6 is configured to absorb the electronic cigarette liquid permeated through the liquid permeating sheet 4; the absorbed electronic cigarette liquid is atomized in the cavity of the atomizing seat 7 to form electronic cigarette smoke. The ceramic atomizing rod 61 of the present invention is made from a porous, permeable ceramic material.

As shown in FIGS. 5 to 10, one supporting vertical groove 52 is provided at the upper end of the atomizing seat in each of the two inner walls at both sides of the vapor outlet 51; that is, two supporting vertical grooves 52 are provided. Each supporting vertical groove 52 is installed with one atomizing unit 6. The atomizing seat 5 further includes an atomizing seat cover 53 provided on its upper-end surface. The atomizing seat cover 53 is provided with cover holes 530 at positions corresponding to the positions of the supporting vertical grooves 52; the ceramic atomizing rods 61 protrude out from the cover holes 530. The lower end surface of the atomizing seat 5 is provided with two legs 54. The upper-end surface of the sealed connection seat 7 is accordingly provided with two grooved portions 74 to accommodate the legs 54 of the atomizing seat 5. A cavity 72 is provided at the center of the upper-end surface of the sealed connection joint 7. A circular groove 73 is provided at the bottom of the cavity 72 at the rim of the through hole 71, the circular groove 73 has an opening facing upwards. The atomizing seat 5 of the present invention can be made from a ceramic material, as ceramic materials tend to have high-temperature resistance, thereby not easily burned by the heating wire 62. In order to have a sealed connective property, the sealed connection seat 7 of the present invention can be made from a high-temperature resistant silicone material.

Figure 11:
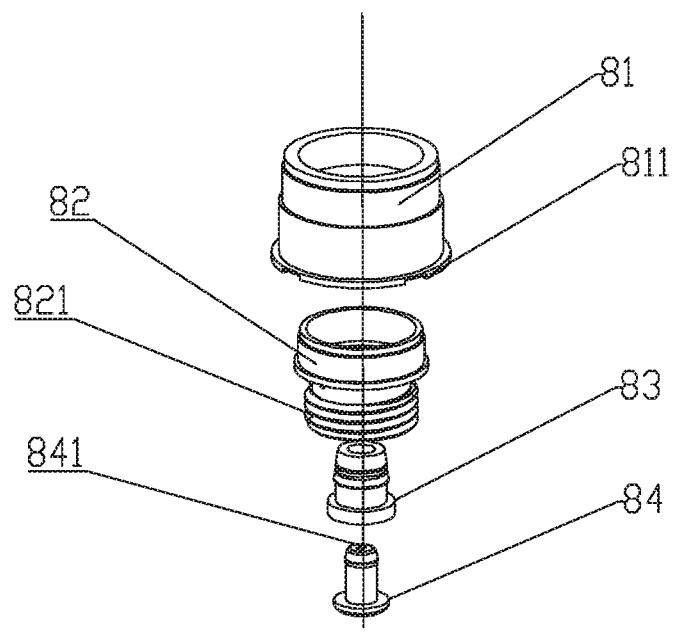
FIG. 11 is an exploded view of a power connector according to the embodiments of the present invention.

As shown in FIGS. 1, 2 and 11, the power connector 8 includes a tubular body 81 which is provided with an annular shoulder 811 at its lower end. An electrode holder 82 is inserted into the tubular body 81 at the upper end of the tubular body 81; a thread 821 is provided at the outer wall of the electrode holder 82 at the lower end of the electrode holder. A radial blocking ring 822 is provided at the inner wall of the tubular body 81. An insulating holder 83 is inserted into a central through hole (not shown in drawings) of the radial blocking ring 822. A nail electrode 84 is inserted into the insulating holder 83; the nail electrode 84 is provided with an electrode through hole 841 for air intake. The two electrodes of the heating wire 62 of the atomizing unit 6 are electrically connected to the nail electrode 84 and the electrode holder 82 respectively and are further electrically connected to the positive and negative electrodes of the electronic cigarette power source.

Embodiment 2

On the basis of the first embodiment described above, the atomization unit 6 is modified: instead of winding around the outer wall of the ceramic atomizing rod 61, the heating wire in this embodiment is provided in the inside of the ceramic atomizing rod 61; the other structures remain the same.

Figure 4:
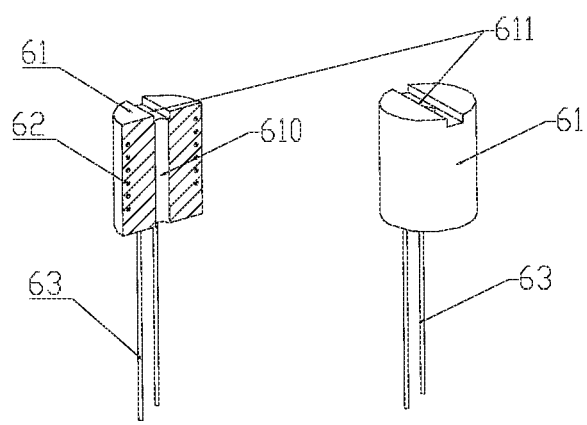
FIG. 4 is a perspective, cross-sectional view and a structural diagram of an atomizing unit according to embodiment 2 of the present invention.
Figure 5:
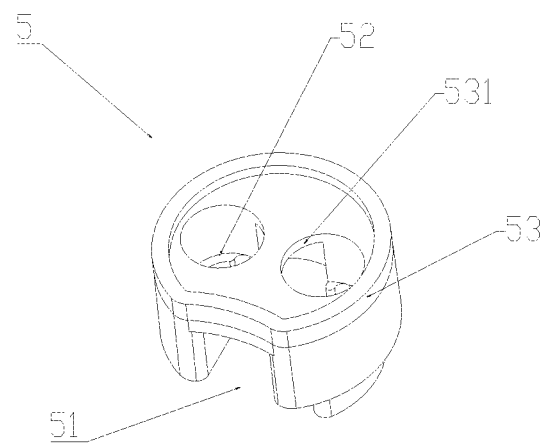
FIG. 5 is a perspective structural view of an atomizing seat according to embodiment 1 of the present invention.
Figure 6:
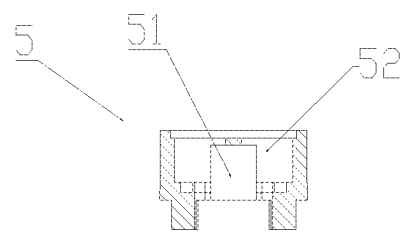
FIG. 6 is a cross-sectional view of an atomizing seat according to embodiment 1 of the present invention.
Figure 7:
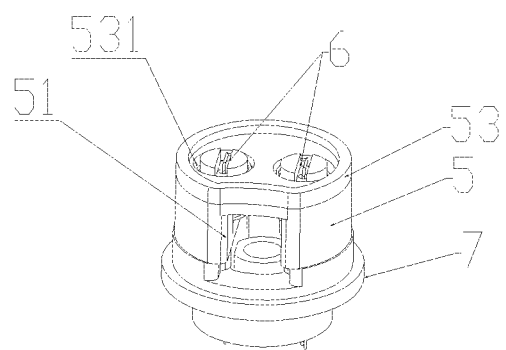
FIG. 7 is a perspective structural view of a sealed connection joint assembled with an atomizing seat and an atomizing unit according to embodiment 1 of the present invention.
Figure 8:
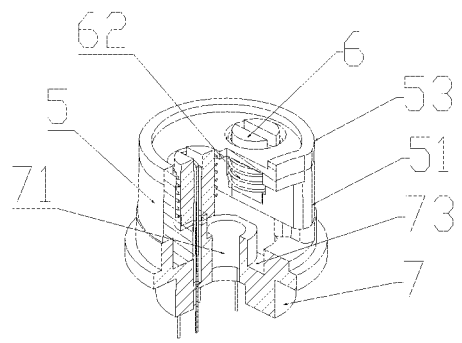
FIG. 8 is a perspective, cross-sectional view of a sealed connection joint assembled with an atomizing seat and an atomizing unit according to embodiment 1 of the present invention.
Figure 9:
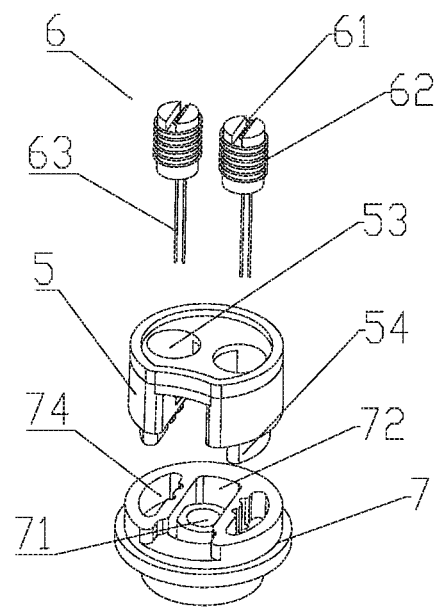
FIG. 9 is an exploded view of a sealed connection joint assembled with an atomizing seat and an atomizing unit according to embodiment 1 of the present invention.
Figure 10:
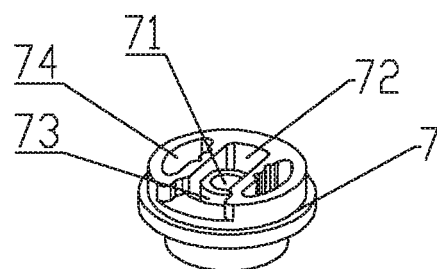
FIG. 10 is a perspective structural view of a sealed connection joint according to the embodiments of the present invention.

As shown in FIG. 4, the ceramic atomizing rod 61 has a cylindrical shape and is provided with an atomizing rod through hole 610 at its central axis. A groove 611 is provided at the upper-end surface of the ceramic atomizing rod 61 along the diameter of the upper-end surface. The heating wire 62 winds around the inside of the ceramic atomizing rod 61 and is fused integrally therewith. The lead wire 63 of the heating wire 62 projects out of the atomizing rod 61 and is led downwards. The atomizing rod through hole 610 and the groove 611 are not used as a passage for the lead wire 63 but are used for venting and the circulation of the cigarette smoke. In this way, the electronic cigarette liquid can penetrate into the ceramic atomizing rod 61 more easily.

Embodiment 3

On the basis of the first embodiment described above, the atomization seat is modified: the number of the supporting vertical grooves is increased from two to three, and the number of the atomization units is increased accordingly. Embodiment 3 is thus designed to further increase the amount of smoke generated simultaneously, effectively improving the atomization effect.

Figure 12:
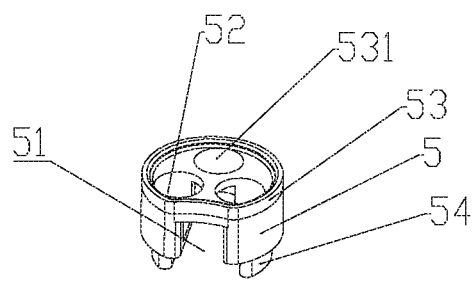
FIG. 12 is a perspective structural view of an atomizing seat according to embodiment 3 of the present invention.
Figure 13:
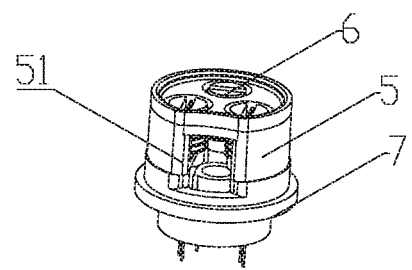
FIG. 13 is a perspective structural view of a sealed connection joint assembled with an atomizing seat and an atomizing unit according to embodiment 3 of the present invention.
Figure 14:
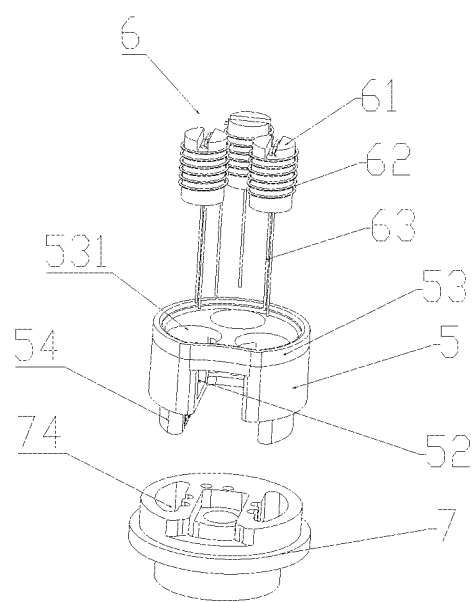
FIG. 14 is an exploded view of a sealed connection joint assembled with an atomizing seat and an atomizing unit according to embodiment 3 of the present invention.

As shown in FIGS. 12-14, one supporting vertical groove 52 is provided at the upper end of the atomizing seat, in each of the three inner walls at both sides of the vapor outlet 51 and opposite the vapor outlet; that is, three supporting vertical grooves 52 are provided. Each supporting vertical groove 52 is installed with one atomizing unit 6. In this embodiment, the heating wires 62 of the three atomizing units 6 are parallelly connected to the power source. As a result, when the atomizer is operating, the amount of smoke generated simultaneously by atomization is greatly increased, effectively improving the atomization effect.

The aforementioned embodiments are only the preferred embodiments of the present invention. All equivalent changes and modifications made within the scope of the claims of the present invention should fall within the scope of protection of the claims of the present invention.

What is claimed is:

1. An electronic cigarette atomizer employing a vertical ceramic atomizing unit, wherein it comprises an outer tube which is provided with a suction hole at its upper end and an opening at its lower end; the electronic cigarette atomizer further comprises a liquid storage cup, a porous supporting sheet, a cigarette liquid permeation sheet, an atomizing seat, an atomizing unit, a sealed connection joint, and a power connector sheathed in the outer tube consecutively from top to bottom; the liquid storage cup is closed at its upper end and opened at its lower end; the porous supporting sheet is horizontally attached to an inner wall of a lower end of the liquid storage cup; the atomizing unit includes a ceramic atomizing rod made from a ceramic material, a heating wire wound around the ceramic atomizing rod, and a lead wire connected to both ends of the heating wire; the atomizing seat is a high-temperature resistant tubular body with a vapor outlet provided at its wall, an upper-end surface of the atomizing seat presses the cigarette liquid permeation sheet tightly against the porous supporting sheet; the ceramic atomizing rod is vertically disposed in the atomizing seat, an upper-end surface of the ceramic atomizing rod is in direct contact with the cigarette liquid permeation sheet and can absorb and conduct electronic cigarette liquid from the cigarette liquid permeation sheet to a portion around which the heating wire is wound; the sealed connection joint is in sealed connection with the atomizing seat and the power connector, the inside of the sealed connection joint is provided with a through hole in an axial direction; the power connector is sheathed a lower end of the outer tube and rests against an inner wall of the outer tube.

2. The electronic cigarette atomizer according to claim 1, wherein one supporting vertical groove is provided in each of two inner walls at both sides of the vapor outlet at an upper end of the atomizing seat; each of the supporting vertical groove is installed with one atomizing unit.

3. The electronic cigarette atomizer according to claim 2, wherein an atomizing seat cover is provided on the upper-end surface of the atomizing seat; the atomizing seat cover is provided with a cover hole at a position corresponding to the supporting vertical groove; the ceramic atomizing rod protrudes from the cover hole.

4. The electronic cigarette atomizer according to claim 2, wherein the heating wire of each of the atomizing unit is parallelly connected to a power source.

5. The electronic cigarette atomizer according to claim 1, wherein one supporting vertical groove is provided at an upper end of the atomizing seat, in each of three inner walls at both sides of the vapor outlet and opposite the vapor outlet; each of the supporting vertical groove is installed with one atomizing unit.

6. The electronic cigarette atomizer according to claim 5, wherein an atomizing seat cover is provided on the upper-end surface of the atomizing seat; the atomizing seat cover is provided with a cover hole at a position corresponding to the supporting vertical groove; the ceramic atomizing rod protrudes from the cover hole.

7. The electronic cigarette atomizer according to claim 5, wherein the heating wire of each of the atomizing unit is parallelly connected to a power source.

8. The electronic cigarette atomizer according to claim 1, wherein the ceramic atomizing rod has a cylindrical shape and is provided with an atomizing rod through hole at its central axis; a groove is provided on the upper-end surface of the ceramic atomizing rod along a diameter of the upper-end surface of the ceramic atomizing rod;

the heating wire winds around an outer wall of the ceramic atomizing rod; the lead wire which is connected to an upper end of the heating wire is disposed in the groove and is led downwards through the atomizing rod through hole; another lead wire is led downwards along the outer wall of the ceramic atomizing rod.

9. The electronic cigarette atomizer according to claim 1, wherein the ceramic atomizing rod has a cylindrical shape and is provided with an atomizing rod through hole at its central axis; a groove is provided on the upper-end surface of the ceramic atomizing rod along a diameter of the upper-end surface of the ceramic atomizing rod;

the heating wire winds around an inside of the ceramic atomizing rod and is fused integrally therewith; the lead wire of the heating wire projects out of the atomizing rod and is led downwards.

10. The electronic cigarette atomizer according to claim 1, wherein the liquid storage cup is provided with a rectangular notch at its lower end wall; an surface of the liquid storage cup is provided with a vapor groove in an axial direction and at the same circumferential position as the rectangular notch; the porous supporting sheet and the cigarette liquid permeation sheet are horizontally disposed and are attached to an inner wall of the liquid storage cup, above the rectangular notch; the atomizing seat is sheathed in the liquid storage cup and rest against an inner wall where the rectangular notch is located; the vapor outlet of the atomizing seat overlaps with the rectangular notch of the liquid storage cup; a heat insulating tube is provided between an outer wall of the liquid storage cup at a position of the rectangular notch, part of an outer wall of the sealed connection joint, part of an outer wall of an upper end of the power connector, and the inner wall of the outer tube.

11. The electronic cigarette atomizer according to claim 1, wherein a lower end surface of the atomizing seat is provided with two legs, an upper-end surface of the sealed connection seat is provided with two grooved portions to accommodate the legs of the atomizing seat; a cavity is provided at a center of the upper-end surface of the sealed connection joint, a circular groove is provided at a bottom of the cavity at a rim of the through hole.

12. The electronic cigarette atomizer according to claim 1, wherein the power connector includes a tubular body which is provided with an annular shoulder at its lower end; an electrode holder which is a hollow tube is inserted into the tubular body at an upper end of the tubular body; a thread is provided at an outer wall of a lower end of the electrode holder; a radial blocking ring is provided at an inner wall of the tubular body; an insulating holder is inserted into a central through hole of the blocking ring; a nail electrode is inserted into the insulating holder, the nail electrode is provided with an electrode through hole at a center thereof.

* * * * *